(12) United States Patent
Grondin et al.

(10) Patent No.: US 11,944,473 B2
(45) Date of Patent: Apr. 2, 2024

(54) ROTATING COLLIMATOR FOR AN X-RAY DETECTION SYSTEM

(71) Applicants: Université Grenoble Alpes, Saint-Martin-d'Hères (FR); Surgiqual Institute, Meylan (FR); Centre Hospitalier Universitaire Grenoble Alpes, La Tronche (FR); Institut Polytechnique de Grenoble, Grenoble (FR); Centre National de la Recherche Scientifique, Paris (FR); Université Claude Bernard Lyon 1, Villeurbanne (FR); École Centrale de Lyon, Ecully (FR); CPE LYON FORMATION CONTINUE ET RECHERCHE, Villeurbanne (FR)

(72) Inventors: Yannick Grondin, Arbin (FR); Philippe Cinquin, Saint-Nazaire-lès-Eymes (FR); Laurent Desbat, Grenoble (FR); Pierrick Guiral, Lyons (FR); Patrick Pittet, Fontaines-Saint-Martin (FR)

(73) Assignees: Université Grenoble Alpes, Saint-Martin-d'Hères (FR); Surgiqual Institute, Meylan (FR); Centre Hospitalier Universitaire Grenoble Alpes, La Tronche (FR); Institut Polytechnique de Grenoble, Grenoble (FR); Centre National de la Recherche Scientifique, Paris (FR); Université Claude Bernard Lyon 1, Villeurbanne (FR); École Centrale de Lyon, Ecully (FR); CPE LYON FORMATION CONTINUE ET RECHERCHE, Villeurbanne (FR)

( * ) Notice: Subject to any disclaimer, the term of this patent is extended or adjusted under 35 U.S.C. 154(b) by 292 days.

(21) Appl. No.: 17/633,891

(22) PCT Filed: Aug. 6, 2020

(86) PCT No.: PCT/EP2020/072208
§ 371 (c)(1),
(2) Date: Feb. 8, 2022

(87) PCT Pub. No.: WO2021/028327
PCT Pub. Date: Feb. 18, 2021

(65) Prior Publication Data
US 2022/0296181 A1 Sep. 22, 2022

(30) Foreign Application Priority Data

Aug. 9, 2019 (FR) ...................................... 1909114

(51) Int. Cl.
*A61B 6/06* (2006.01)
*A61B 6/40* (2024.01)

(52) U.S. Cl.
CPC . *A61B 6/06* (2013.01); *A61B 6/40* (2013.01)

(58) Field of Classification Search
CPC ...... A61B 6/06; A61B 6/08; G01N 2223/316; G01N 2223/313; G01N 2223/314; G01N 2223/33
See application file for complete search history.

(56) References Cited

U.S. PATENT DOCUMENTS 6,490,475 B1  12/2002  Seeley et al.
7,065,393 B2   6/2006  Sati et al.

FOREIGN PATENT DOCUMENTS

FR   2841118 A1  12/2003
FR   3028039 A1   5/2016
(Continued)

OTHER PUBLICATIONS

Foreign Communication from a Related Counterpart Application, International Search Report dated Oct. 9, 2020, International Application No. PCT/EP2020/072208 filed on Aug. 6, 2020.

(Continued)

*Primary Examiner* — Don K Wong
(74) *Attorney, Agent, or Firm* — Conley Rose P.C.

(57) ABSTRACT

Collimation device for an X-ray detection system, the collimation device comprising: a collimator comprising a substantially planar support made of a material with partial or zero radiotransparency, the support being rotatably movable about an axis of rotation (Δ) which passes through the support and which is perpendicular to a first face of the (Continued)

support which acts as an X-ray plane of incidence referred to as the main plane of the support (P), the support (D) being provided on the first face with a slit which is completely transparent to X-rays and which is configured to generate an X-ray flow when the collimator is exposed to an X-ray source, the slit extending longitudinally in the main plane of the support along an axis located at a non-zero distance (d) from the axis of rotation (Δ), the slit extending through the entire thickness of the support.

23 Claims, 10 Drawing Sheets

(56) References Cited

FOREIGN PATENT DOCUMENTS

| | | |
|---|---|---|
| FR | 3042881 A1 | 4/2017 |
| GB | 1387442 A | 3/1975 |
| WO | WO-2012174265 A1 * 12/2012 | ........... G01V 5/0025 |
| WO | 2016071645 A1 | 5/2016 |
| WO | 2017072125 A1 | 5/2017 |
| WO | 2021028327 A1 | 2/2021 |

OTHER PUBLICATIONS

Foreign Communication from a Related Counterpart Application, Written Opinion dated Oct. 9, 2020, International Application No. PCT/SG2017/050610 filed on Aug. 6, 2020.

A. Legrand, et al. "An ultrafast mechanical shutter for X-rays" Nuclear Instruments and Methods in Physics Research Section A: Accelerators, Spectrometers, Detectors and Associated Equipment, vol. 275, No. 2, Feb. 15, 1989 (Feb. 15, 1989), pp. 442-446 DOI: 10.1016/0168-9002(89)90722-5 ISSN: 0168-9002, XP055001570.

* cited by examiner

| Material | K-edge keV | 40keV mm | 60keV mm | 80keV mm | 100keV mm |
|---|---|---|---|---|---|
| NaI | 33.2 | 0.43 | 1.3 | 2.7 | 4.9 |
| CsI | 33.2 | 0.29 | 0.8 | 1.8 | 3.3 |
| CdWO$_4$ | 69.5 | 0.33 | 0.9 | 0.5 | 0.9 |
| BGO | 90.5 | 0.38 | 1.1 | 2.2 | 1.1 |
| LSO | 63.3 | 0.55 | 1.6 | 0.7 | 1.3 |
| PreLude (LYSO) | 63.3 | 0.58 | 1.65 | 0.8 | 1.4 |

| Position | Δt | π−(beta-alpha) | r |
|---|---|---|---|
| P1 | 26.1ms | 18.7° | 12.9mm |
| P2 | 23.7ms | 32.5° | 7.2mm |
| P3 | 20.3ms | 54.1° | 4.4mm |

| Position | Δt | π−(beta-alpha) | r |
|---|---|---|---|
| P1 | 17.1ms | 19.5° | 11.8mm |
| P2 | 15.7ms | 32.2° | 7.2mm |
| P3 | 13.3ms | 54.5° | 4.4mm | ns # ROTATING COLLIMATOR FOR AN X-RAY DETECTION SYSTEM

CROSS-REFERENCE TO RELATED APPLICATIONS

The present application is a filing under 35 U.S.C. 371 as the National Stage of International Application No. PCT/EP2020/072208, filed Aug. 6, 2020, entitled "ROTATING COLLIMATOR FOR AN X-RAY DETECTION SYSTEM," which claims priority to French Application No. 1909114 filed with the Intellectual Property Office of France on Aug. 9, 2019, both of which are incorporated herein by reference in their entirety for all purposes.

TECHNICAL FIELD AND PRIOR ART

The present application relates to the field of X-ray detection systems, and more particularly relates to the field of spatially locating elements in an X-ray detection system.

The present application also applies to X-ray imaging, in particular to "interventional" imaging in which it is sought to precisely determine the position of a tool at the same time as images are being acquired, for example during a surgical intervention or an operation performed using this tool.

Document FR 2 841 118 presents an X-ray imaging system comprising a means for determining the position of a radiographic unit using a test pattern fixed to an object of which an image is acquired.

In such a system, the image of the test pattern interferes with that of the object that it is desired to study.

Document U.S. Pat. No. 6,490,475 presents a fluoroscopic system in which the positions of elements of the system are determined using markers. Digital processing is then carried out in order to be able to remove the trace of these markers from the final image.

Document U.S. Pat. No. 7,065,393 relates to a method for calibrating an X-ray imaging system using inertial sensors arranged on different elements of the system.

This type of sensor is often subject to a substantial build-up of errors and low accuracy and can therefore present problems with regard to reliably determining the position of an element equipped with sensors in an X-ray imaging system.

Patent application FR3042881 presents a device for X-ray imaging comprising a rotating collimator, comprising two slits. Such a device makes it possible to reliably determine the position in a given frame of reference of an element provided with X-ray sensors which are intended to receive X-ray beams coming from the slits in the collimator.

The present application aims in particular to simplify the device of patent application FR3042881.

To that end, the present application relates, according to a first aspect, to a collimation device for an X-ray detection system, the collimation device comprising:
a collimator comprising a substantially planar support made of a material with partial or zero radiotransparency, the support being rotatably movable about an axis of rotation which passes through the support and which is perpendicular to a first face of the support which acts as an X-ray plane of incidence referred to as the main plane of the support, the support being provided on the first face with a single slit which is completely transparent to X-rays and which is configured to generate an X-ray flow when the collimator is exposed to an X-ray source, the slit extending longitudinally in the main plane of the support along an axis located at a non-zero distance from the axis of rotation, said slit extending through the entire thickness of the support.

Such a single-slit collimator allows a simplified implementation of the collimation device.

In one or more embodiments, the slit has a projection of rectangular or trapezoidal shape in the main plane of the support.

Another subject of the present application relates, according to a second aspect, to an X-ray detection system, the detection system comprising:
an X-ray source configured to emit an X-ray beam;
a collimation device according to the first aspect, placed so as to receive the X-ray beam on the plane of incidence of the support of the collimation device;
a drive device configured to rotate the support of the collimation device about its axis with a fixed angular speed of rotation;
at least one X-ray detection element placed in an acquisition field opposite the support with respect to the X-ray source so as to acquire X-rays when a portion of the X-ray beam, passing through the slit in the support from the first face of the support to the opposite face, reaches the detection element in question during the rotation of the support.

In one or more embodiments, one detection element from among said at least one X-ray detection element is configured to detect X-rays passing through the slit at two successive times while the support is rotating, a first time corresponding to a first angular position of the slit and a second time corresponding to a second angular position of the slit, the first and second angular positions defining in the main plane of the support a point of intersection corresponding to the projected position in the main plane of the support of the detection element; the detection system comprising a processing unit configured to determine the projected position in the main plane of the support of the detection element from the first and second angular positions. Thus, for each rotation (complete revolution), two successive times and therefore two angular positions are obtained. The first and second angular positions are, for example, determined from the two successive times and from the angular speed of rotation of the support.

In another embodiment, the determination of the first and second angular positions involves an optical fork and the X-ray detection system further comprises a second support, secured to the support or forming an integral part of the support, comprising a series of N windows uniformly distributed angularly around a circular periphery centered with respect to the axis of rotation of the support, said series of N windows comprising a reference window of different size from the other windows, the other windows being indexed with respect to this reference window.

In this case, one detection element from among said at least one X-ray detection element is configured to detect X-rays passing through the slit for first and second angular positions of the second support defining in the main plane of the support a point of intersection corresponding to the projected position in the main plane of the support of the detection element. In this embodiment, the X-ray detection system comprises an optical fork, the optical fork being provided with an emitter configured to emit a light wave and a detector configured to detect the light wave, said fork being configured to generate electrical pulses when, on any one of the windows passing between the emitter and the receiver, the receiver receives the light wave, the first and second angular positions each corresponding to the passage of a window. The processing unit is then configured to determine the first and second angular positions based on the indexes of the two windows that have produced the electrical pulses which are temporally closest to the two successive times for which the detection by the detection element has taken place.

In one or more embodiments, the processing unit is configured to determine the distance between a plane containing the detection element and parallel to the main plane of the support and the X-ray source from a duration of irradiation of the detection element, from the angular speed of rotation of the support, from the distance between the X-ray source and the support, from the width of the slit and from the distance between the intersection of the axis of rotation of the support and the projected position in the main plane of the support.

In one or more embodiments, the X-ray source is a pulsed source configured to emit X-rays in emission cycles composed of two modes used alternately, one being an X-ray emission mode, the other being an X-ray non-emission mode. One detection element from among the X-ray detection elements is then configured to detect X-rays passing through the slit in a manner synchronized with the X-ray emission cycles.

In one or more embodiments, in the case where the X-ray source is a pulsed source, the support of the collimation device according to the first aspect of the present application is made of an X-ray scintillator material. The support is then able to emit scintillation photons when the support is exposed to the X-ray source. The detection system according to the second aspect of the present application further comprises a photodiode configured to detect the scintillation photons and issue a photocurrent resulting from the detected scintillation photons so as to trigger the detection and acquisition by the detection element of X-rays passing through the slit in the support.

In this case, the processing unit can be configured to use the photocurrent issued by the photodiode to automatically feedback-control the angular speed of rotation of the support with respect to the duration of the pulses from the pulsed source. The speed of rotation is such that the collimator makes at least one revolution over the duration of a pulse.

The present application relates, according to a third aspect, to an X-ray imaging system comprising an X-ray detection system according to the second aspect, a plurality of acquisition elements forming an acquisition matrix placed in an acquisition field of the imaging system, each acquisition element of the acquisition matrix being configured to acquire an X-ray flow build-up when the support of the collimator of the detection system is rotating about its axis, the acquisition matrix being configured to acquire a radiographic image on the basis of the acquisitions made respectively by the acquisition elements constituting the matrix during a given time period.

In one or more embodiments, the X-ray imaging system further comprises a planar diaphragm placed between the X-ray source and the single-slit rotating support, delimiting a field of view whose projection on the acquisition matrix does not exceed the size of the acquisition matrix. This planar diaphragm makes it possible to avoid illuminating regions other than that comprising the plurality of acquisition elements forming an acquisition matrix and spatially limits the radiation from the X-ray source so as, for example, to avoid illuminating a practitioner or operator using the X-ray imaging system.

In one or more embodiments, the X-ray source is a pulsed source configured to emit X-rays in emission cycles composed of two modes used alternately, one being an X-ray emission mode, the other being an X-ray non-emission mode. In this case, the acquisition matrix is configured to acquire radiographic images in a manner synchronized with the X-ray emission cycles.

When the X-ray source is a pulsed source, the support is made of an X-ray scintillator material, said support being able to emit scintillation photons when the support is exposed to the X-ray source, said imaging system then further comprising a photodiode configured to detect the scintillation photons and issue a photocurrent resulting from the detected scintillation photons so as to trigger the acquisition by the acquisition matrix of at least one of the radiographic images.

In this case, the processing unit can be configured to use the photocurrent issued by the photodiode to automatically feedback-control the angular speed of rotation of the support with respect to the duration of the pulses from the pulsed source.

Another subject of the present application relates, according to a fourth aspect, to a method for locating a detection element of an X-ray detection system according to the second aspect, the method comprising the following steps:
   rotating the support of the collimation device about its axis of rotation at a fixed angular speed of rotation;
   exposing the support to an X-ray beam from the X-ray source during the rotation of the support;
   the detection element detecting X-rays passing through the slit in the support at two successive times, a first time corresponding to a first angular position of the slit and a second time corresponding to a second angular position of the slit,
   the processing unit determining the projected position in the main plane of the support of the detection element based on the first and second angular positions.

The first and second angular positions can be determined from the two successive times and additionally from the angular speed of rotation of the support.

In one or more configurations, where the X-ray detection system according to the second aspect comprises a second support and an optical fork, the method comprises the following steps:
   rotating the support of the collimation device about its axis of rotation at a fixed angular speed of rotation;
   exposing the assembly formed by the support and the second support to an X-ray beam from the X-ray source during the rotation of the support;
   detecting electrical pulses produced when, on any one of the windows passing between the emitter and the receiver of the optical fork, the receiver receives the light wave;
   the detection element detecting X-rays passing through the slit in the support for a first angular position of the second support and a second angular position of the second support;
   the processing unit determining the projected position in the main plane of the support based on the first and second angular positions, the first and second angular positions being obtained on the basis of the indexes of the two windows that have produced the electrical pulses which are temporally closest to the two successive times for which the detection by the detection element has taken place.

In one or more embodiments, the locating method according to the fourth aspect further comprises a step of determining, by the processing unit, the distance between a plane passing through the detection element and parallel to the collimator and the X-ray source from a duration of irradiation of the detection element, from the angular speed of rotation of the support, from the distance between the X-ray source and the support and from the width of the slit.

In the case where the X-ray source is a pulsed source, and where the detection system comprises a photodiode, the processing unit uses the photocurrent issued by the photodiode to automatically feedback-control the angular speed of rotation of the support (V) with respect to the duration of the pulses from the pulsed source. This makes it possible to ensure a speed of rotation at least 360° over the duration of a pulse.

Another subject of the present application relates to an X-ray imaging method implementing the X-ray imaging system according to the second aspect, said imaging method comprising the following steps:

rotating the support of the collimation device of the imaging system about its axis of rotation at a fixed angular speed of rotation;

exposing the support to an X-ray beam from the X-ray source during the rotation of the support;

the acquisition elements of the acquisition matrix detecting X-rays during the rotation of the support;

acquiring a radiographic image on the basis of the detections made respectively by the acquisition elements of the acquisition matrix during a given time period.

In the case where the X-ray imaging method is implemented by an X-ray imaging system comprising a pulsed source, and in which the support of the collimator is made of an X-ray scintillator material, and is able to emit scintillation photons when the support is exposed to the X-ray source, said X-ray imaging system further comprising a photodiode configured to detect the scintillation photons and issue a photocurrent resulting from the detected scintillation photons so as to trigger the acquisition by the acquisition matrix of at least one of the radiographic images, the method comprises the following steps:

rotating the support of the collimation device of the imaging system about its axis of rotation at a fixed angular speed of rotation;

exposing the support to an X-ray beam from the X-ray source during the rotation of the support;

the acquisition elements of the acquisition matrix detecting X-rays during the rotation of the support;

the support emitting scintillation photons;

the photodiode detecting the scintillation photons, the photodiode issuing a photocurrent resulting from the detected scintillation photons so as to trigger the acquisition by the acquisition matrix of at least one of the radiographic images, acquiring a radiographic image on the basis of the detections made, respectively, by the acquisition elements of the acquisition matrix during a given time period.

In this case, the processing unit can use the photocurrent issued by the photodiode to automatically feedback-control the angular speed of rotation of the support with respect to the duration of the pulses of the pulsed source such that the acquisition of a radiographic image on the basis of the detections made, respectively, by the acquisition elements of the acquisition matrix is temporally windowed over the X-ray emission modes of the emission cycles of the pulsed source. The image can be constructed by building up the signals that are detected over one or more time windows.

Other advantages and features of the present application will become apparent from the following description, given by way of non-limiting example and with reference to the appended figures.

Figure 5:
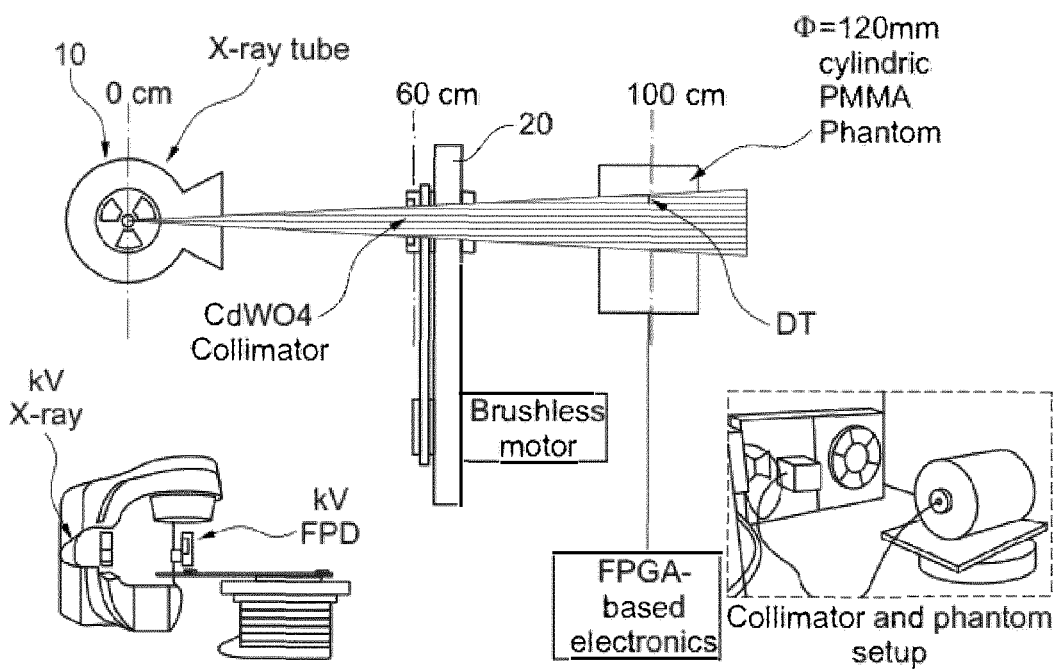

FIG. 5 schematically shows an X-ray detection system according to one exemplary embodiment.

Figure 6A:
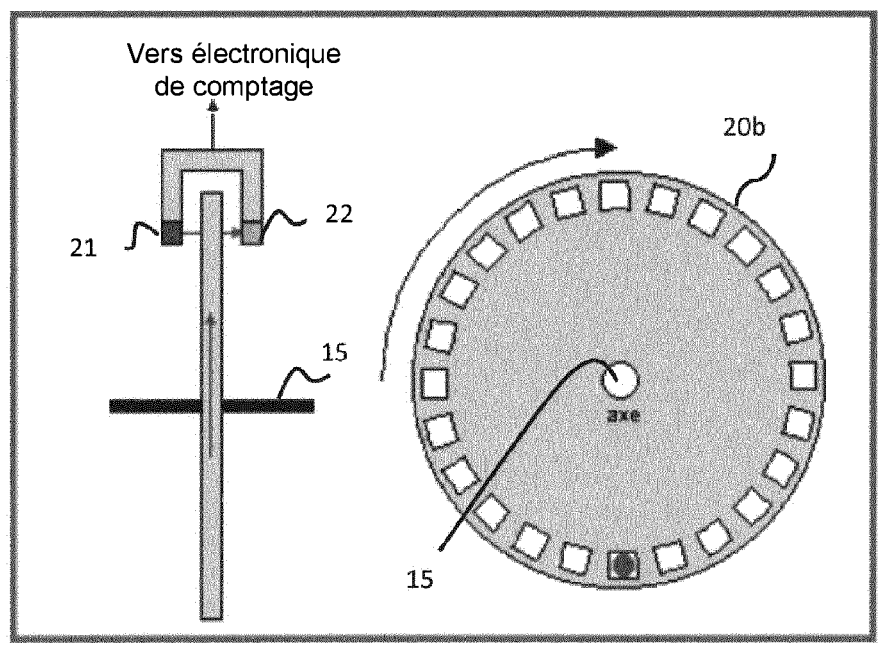

FIG. 6A is a diagram showing the principle of an optical fork.

Figure 6B:
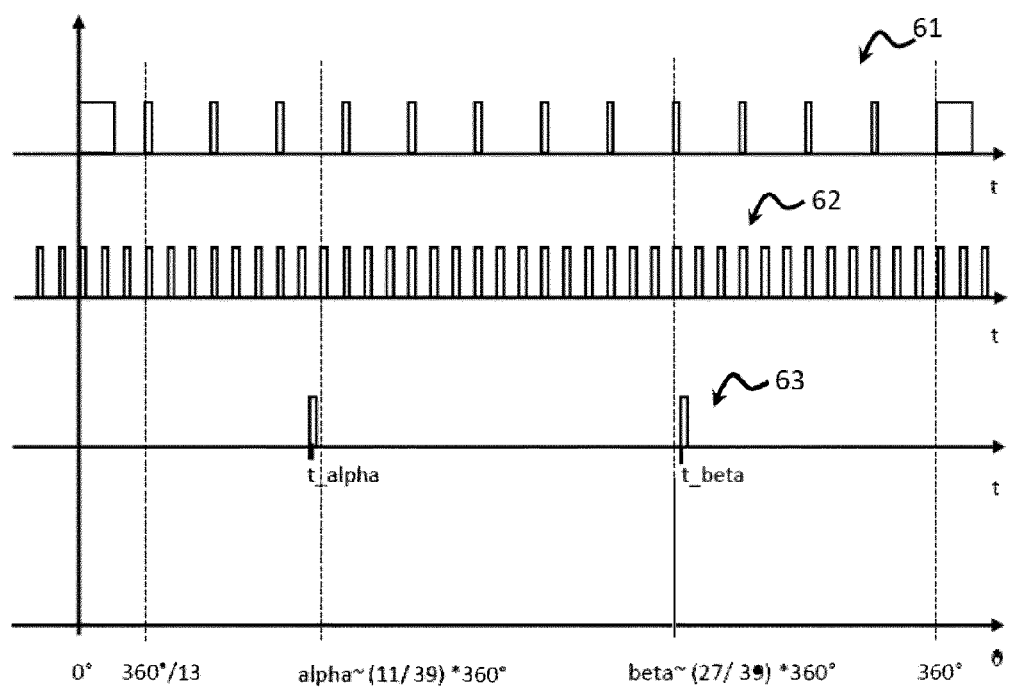
Figure 7:
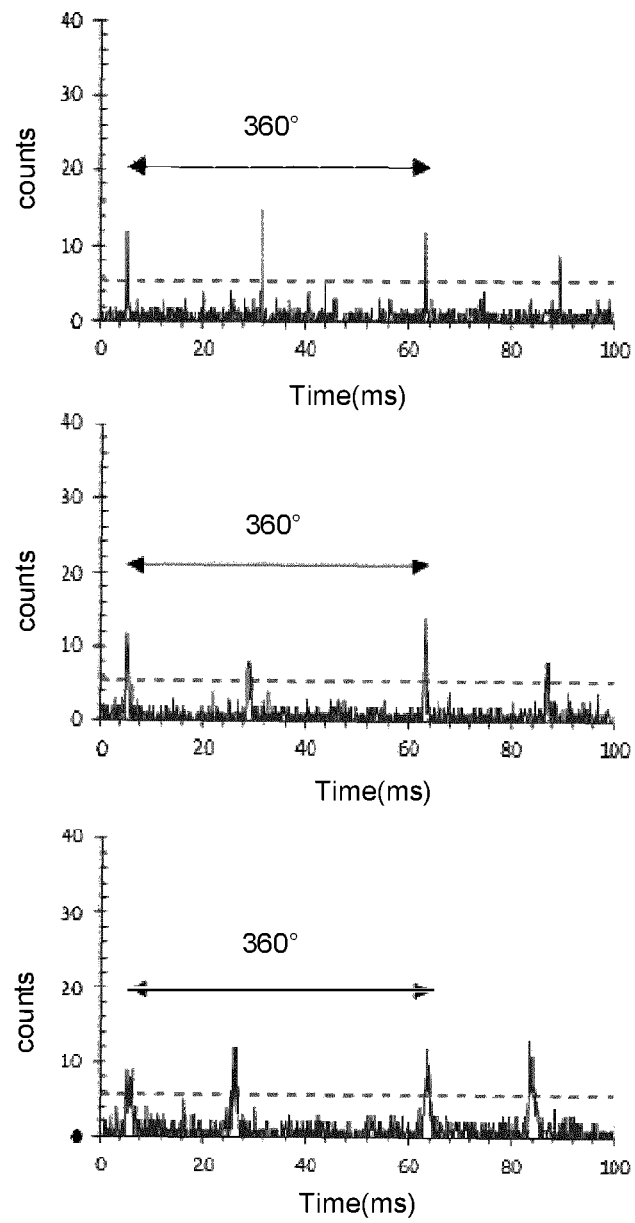

FIG. 6B schematically illustrates the operating principle of the phase-locked loop FIG. 7 shows measurement results for times t_alpha and t_beta, for three different positions of an X-ray detection element placed in a phantom body.

Figures 8, 9:
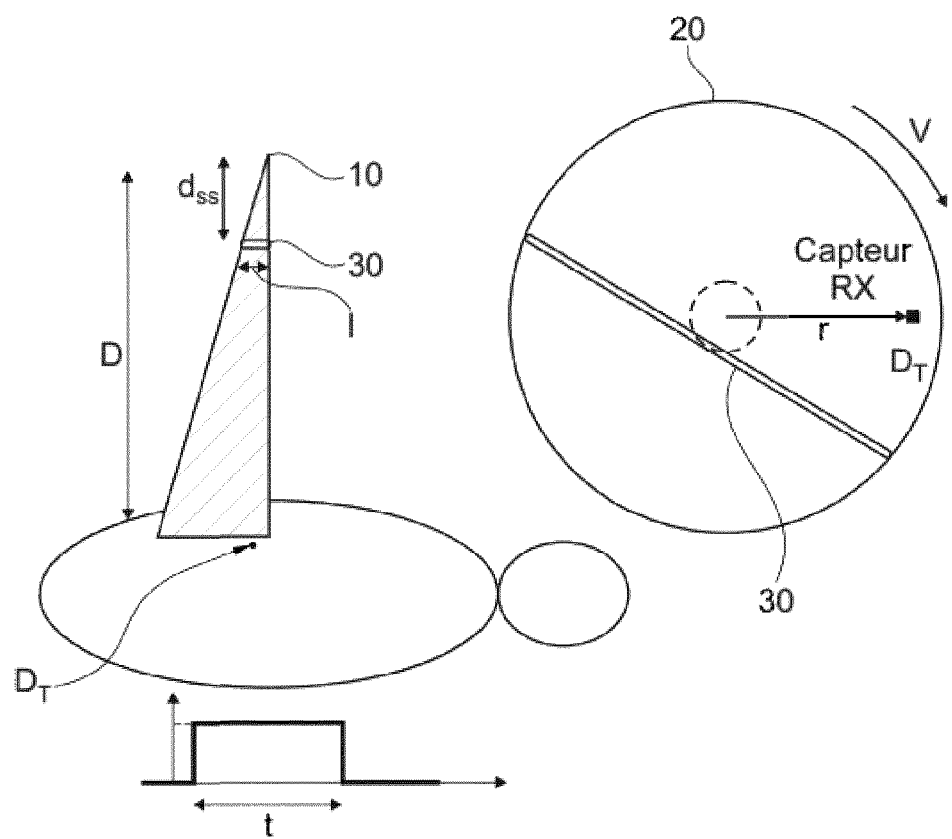

FIG. 8 shows various results for locating a detection element that are obtained via one embodiment of a locating method.

FIG. 9 illustrates the irradiation of a detection element by a flow coming from the slit in a collimation device according to one exemplary embodiment.

Figure 10:
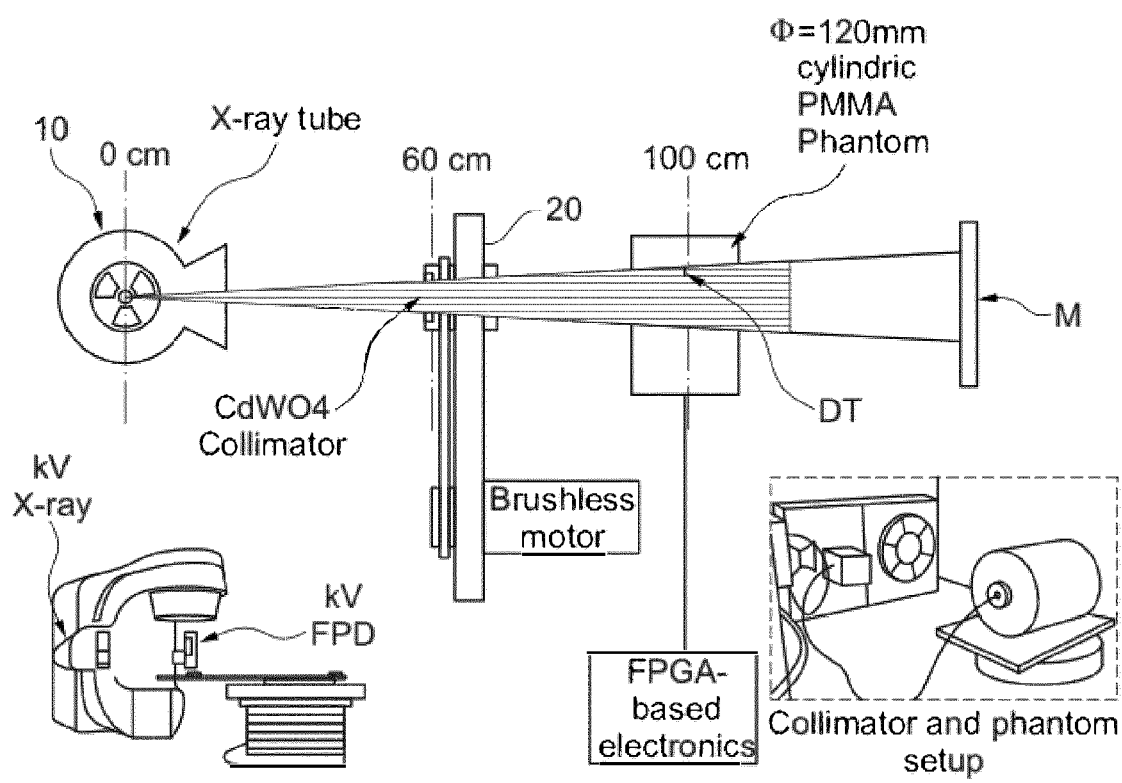

FIG. 10 schematically shows an X-ray imaging system according to one exemplary embodiment.

Figure 11:
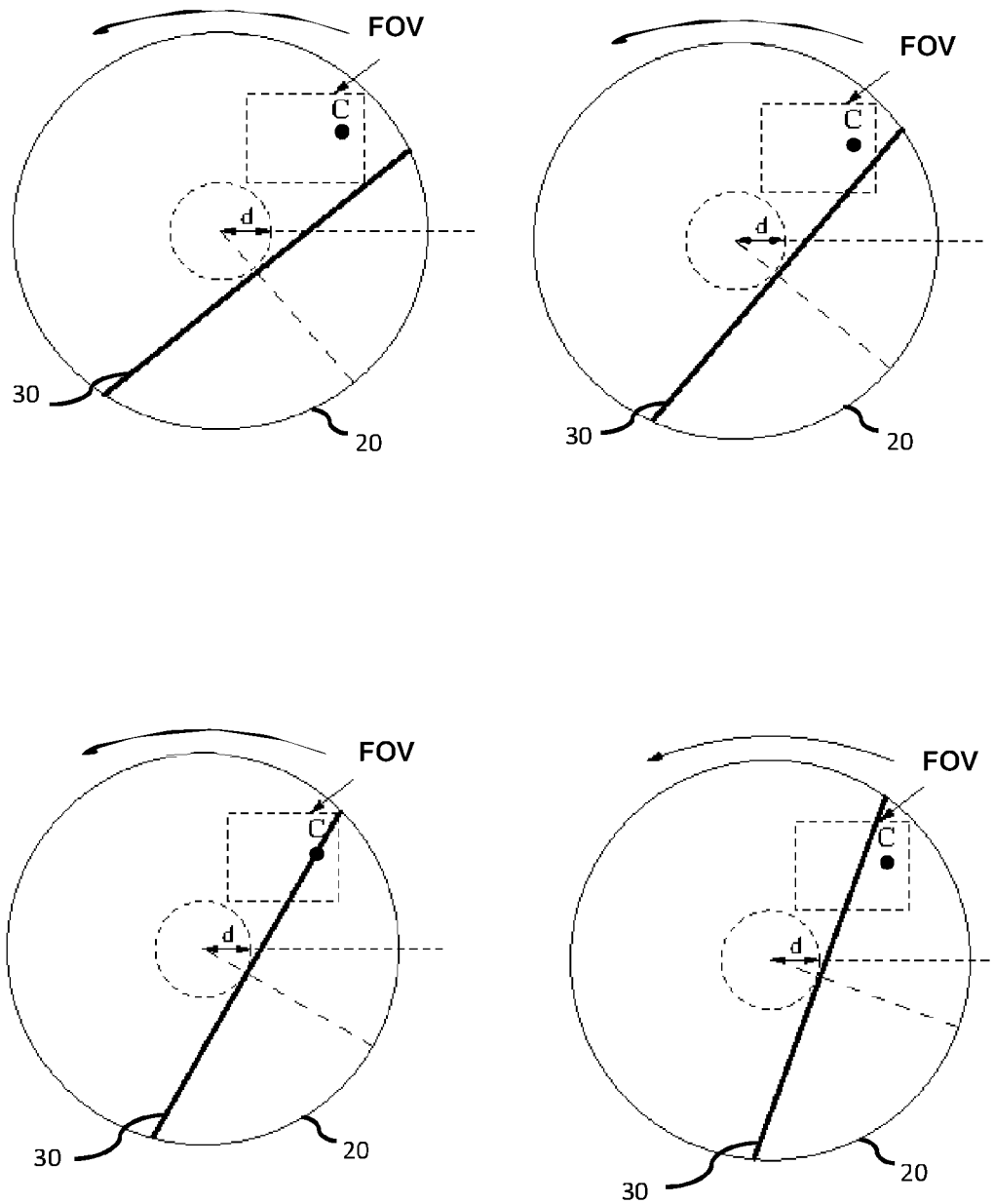

FIG. 11 illustrates the scanning of a field of view by a succession of X-ray flows that are produced by rotating a collimation device according to one exemplary embodiment.

Figure 12:
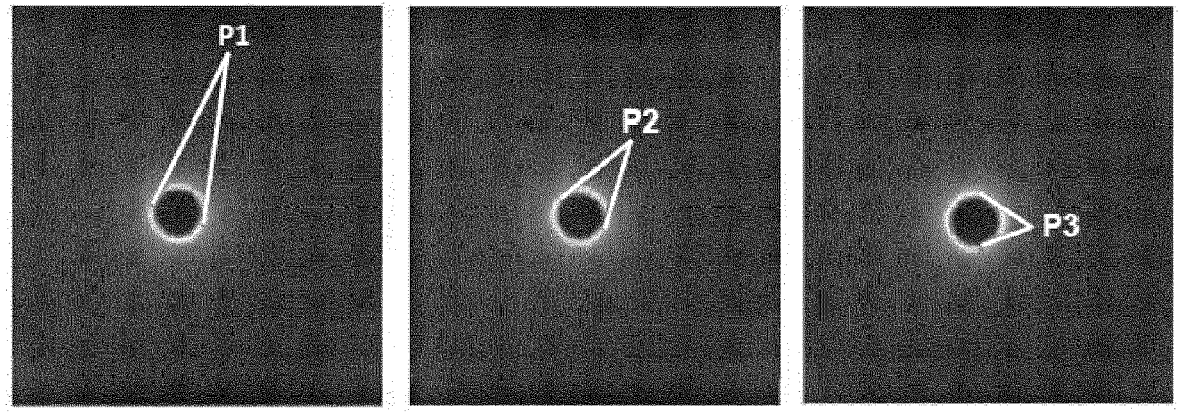

FIG. 12 shows three radiographic images obtained via one embodiment of an X-ray imaging method.

Figure 13:
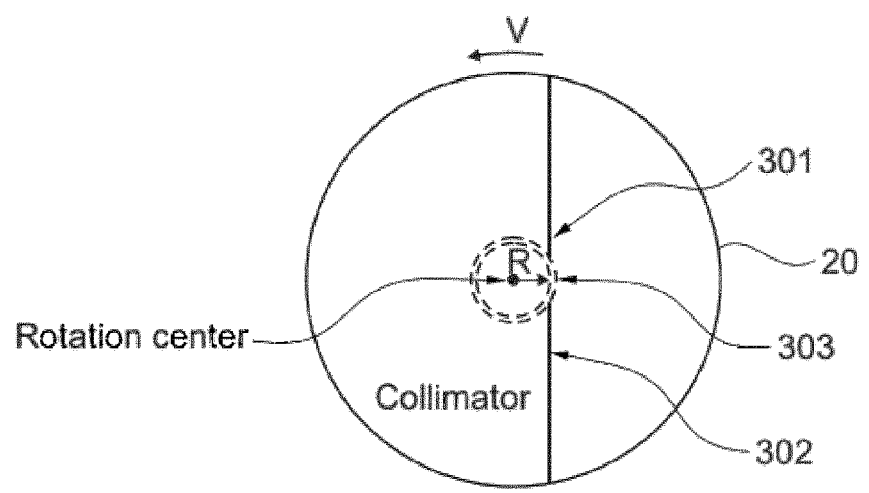

FIG. 13 illustrates one embodiment of a slit in a collimation device according to one exemplary embodiment.

Figure 14A:
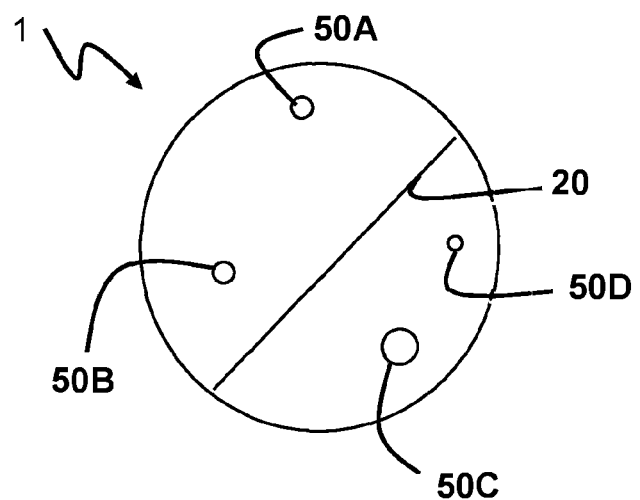
Figure 14B:
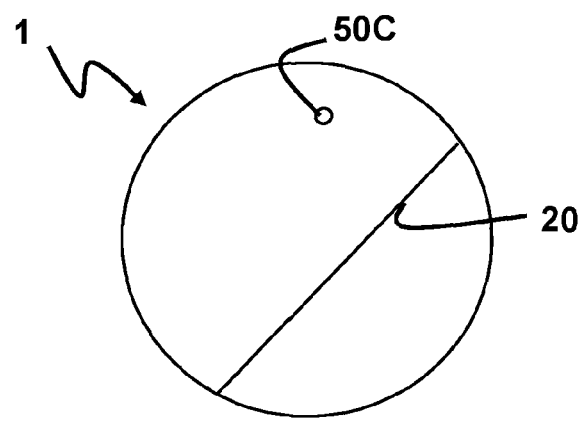

FIG. 14A and FIG. 14B each illustrates one embodiment of a collimation device according to one exemplary embodiment allowing calibration.

Figures 1, 2:
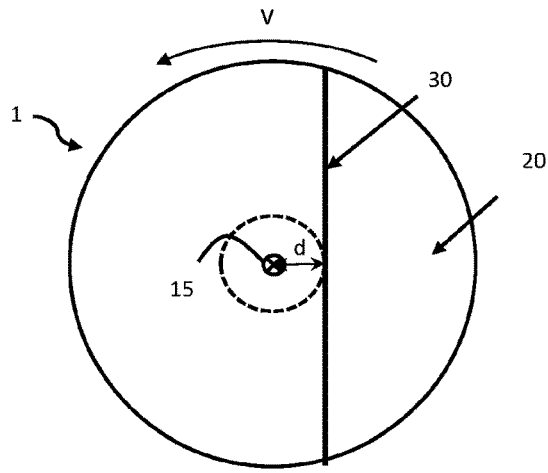
FIG. 1 shows a collimation device according to one embodiment.
FIG. 2 illustrates the concept of partial radiotransparency with quantitative data relating to different materials.

FIG. 1 shows a collimation device 1 for an X-ray detection system 2. The collimation device 1 comprises a collimator comprising a substantially planar support 20 made of a material with partial or zero radiotransparency. In FIG. 1, the support 20 is shown in the form of a disk, but the support could take any other two-dimensional form. The support 20 can be rotatably movable about an axis Δ 15 of rotation passing through the support 20 and perpendicular to a first face of the support 20 which acts as an X-ray plane of incidence and is referred to as the main plane of the support P. The support 20 is provided with a slit 30 extending longitudinally in the main plane of the support P and through the entire thickness e of the support 20. The slit 30 is completely transparent to X-rays and is located at a non-zero distance d from the axis of rotation Δ 15. The slit can be rectangular in shape, as in FIG. 1. In this case, the slit has a width I. The slit can also be trapezoidal in the main plane of the support.

A collimation device (or collimator) makes it possible to spatially limit an incident beam. In the context of the application described in this document, the beam upstream of the collimation device is, for example, of the "cone-beam" type and the beam downstream of the collimation device is of the "fan-beam" type. The collimated beam at the output of the collimation device scans the space in order in particular to allow the position in space of a detection element to be determined (for example, the position of a sensor attached to a tool that is to be located).

In practice, the slit has a certain thickness (corresponding to that of the support) and can have a 3D shape corresponding to a rectangular parallelepiped or else have a non-rectangular cross section (in the plane perpendicular to the support). For example, an inclination can be provided as a function of the divergence of the X-ray beam emanating from the X-ray source as explained in patent application FR3042881 with regard to FIGS. 2A and 2B.

The term "partial radiotransparency" is understood to mean a non-zero percentage attenuation of a flow of mono-energetic photons. This percentage depends on the material used for the support 20 and the thickness of the support 20. FIG. 2 shows various values of thicknesses (in mm) of materials which, for a given photon energy (in keV), make it possible to obtain a 95% attenuation of a flow of incident mono-energetic photons. For example, a support 20 made of $CdWO_4$ material with a thickness of 0.9 mm allows 95% attenuation of the flow of a beam of mono-energetic photons with an energy of 100 keV.

The expression "fully radiotransparent" means that the slit 30 exhibits no absorption, or no significant absorption, of the X-ray beam. For example, the thickness or the material, or a combination of these two parameters, of the slit defined in the support can be chosen to obtain a fully radiotransparent slit 30. This will be the case, for example, if the slit corresponds to an opening in the support (i.e. it is filled with air).

What is meant by "zero radiotransparency" is total opacity to X-rays. More precisely, what is meant by "zero radiotransparency" is a percentage attenuation of a flow of mono-energetic photons of more than 99 percent. What is meant by "partial radiotransparency" is a percentage attenuation of a flow of mono-energetic photons of between 1 and 99 percent, for example higher than 10 percent, or higher than 50 percent. A percentage attenuation higher than 80 percent makes it possible to obtain a good compromise between the irradiation level and the quality of the images that can be acquired. In such a case, the collimator strongly absorbs the X-ray beam.

Figure 3:
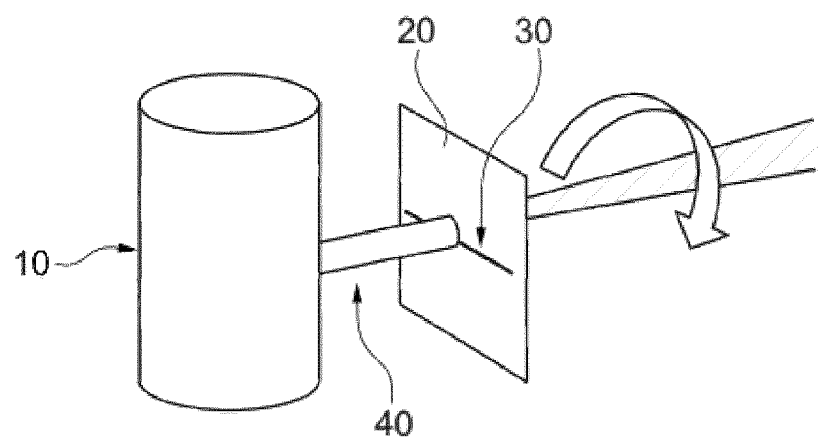
FIG. 3 is a simplified representation of an X-ray detection system.
Figure 3:
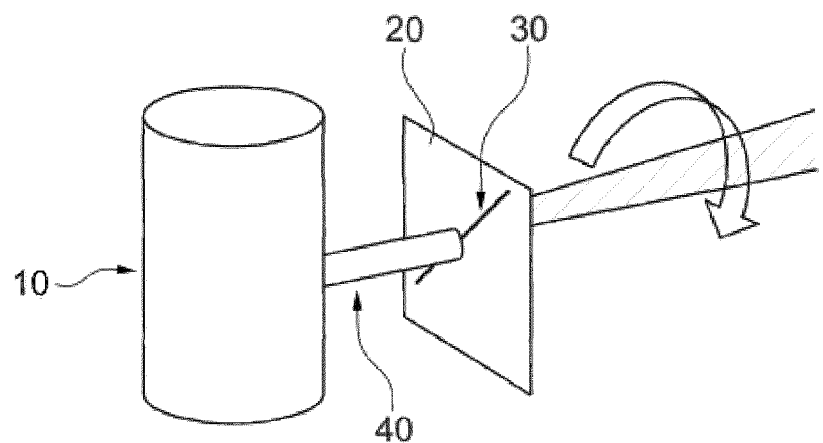

FIG. 3 is a representation of an X-ray detection system 2. The X-ray detection system 2 comprises:
- an X-ray source 10 generating an X-ray beam,
- a collimation device 1 according to any one of the embodiments described in the present application,
- a drive device configured to rotate the support 20 of the collimation device 1 about its axis of rotation Δ with a fixed angular speed V,
- at least one X-ray detection element placed in an acquisition field opposite the support 20 with respect to the X-ray source 10.

The detection element is placed so as to acquire X-rays when an X-ray flow (corresponding to a portion of the beam generated by the X-ray source 10) passes through the slit 30, from the plane of incidence to the opposite face of the support of the collimation device, and reaches the considered detection element. The geometry of this X-ray flow is dependent on the shape of the slit 30. For example, the geometry of the X-ray flow can be fan geometry. For example, the X-ray flow can be a planar flow.

The X-ray source 10 is, for example, an X-ray tube operating at inter-electrode voltages of between 40 and 125 kV.

In a first embodiment, when the support 20 is rotated by the drive device, and the collimation device 1 is exposed to X-rays from the X-ray source 10 while the support 20 is rotating, a detection element DT intercepts at two times, a first time t_alpha and a second time t_beta, respectively, a high-intensity X-ray flow produced by the slit 30. The first time t_alpha corresponds to a first angular position alpha and the second time t_beta corresponds to a second angular position beta. The first and second angular positions alpha and beta of the slit 30 define in the main plane of the support P a point of intersection C corresponding to the projected position PT in the main plane of the support 20 of the detection element DT. The point of intersection C also corresponds to the intersection of the line of intersection of the planes defined by the two X-ray flows intercepted by the detection element DT with the main plane of the support P.

Thus, determining the position of the point of intersection C is possible by using a rotating support having only one slit, off-center with respect to the axis of rotation of the collimator. During a rotation of the support, the detection element DT is irradiated twice by the X-ray beam passing through the slit in two different planes of irradiation. The intersection of these two planes is a straight line connecting the X-ray source to the detection element DT. It is thus possible to locate it. The assumption is made here that the detection element DT does not move during a rotation of the support because the speed of rotation of the rotating collimator is sufficiently high (for example 1 revolution per 25 ms) and the speed of movement of the detection element DT is sufficiently low that the displacement of the detection element DT during one revolution of the collimator is negligible.

Figure 4:
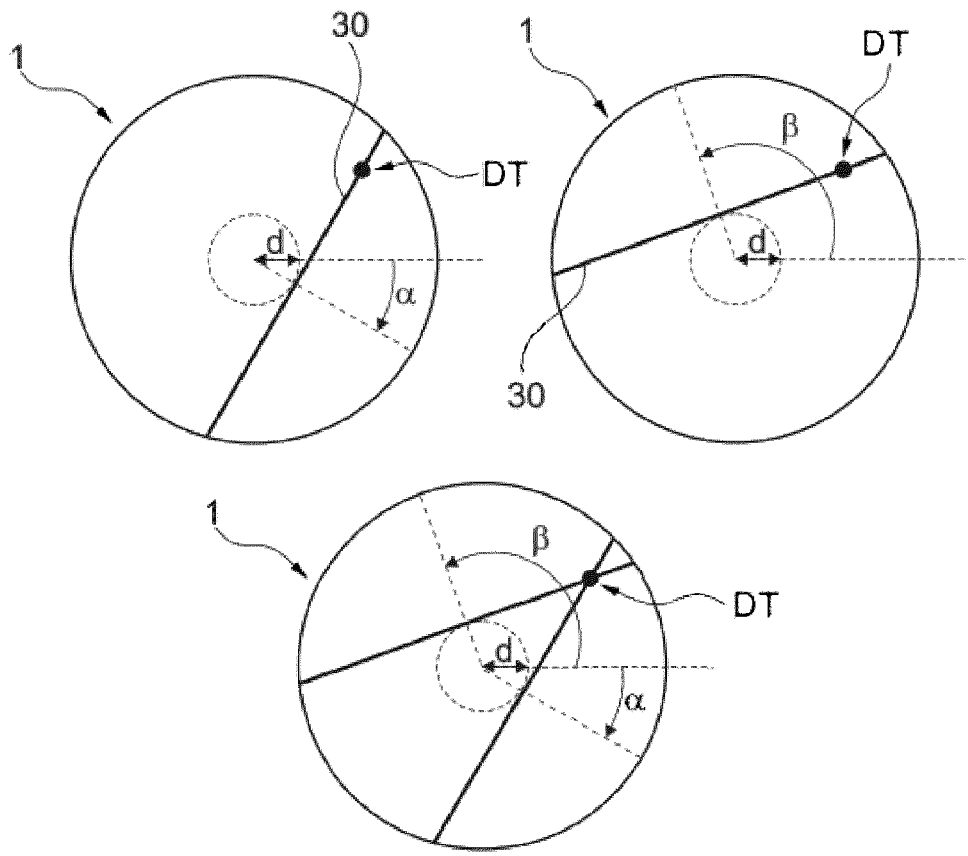
FIG. 4 illustrates aspects of calculating a position that is projected in a plane of a support of a collimation device.

FIG. 4 schematically shows the first and second angular positions alpha and beta for which the detection element DT intercepts the X-ray flows produced by the slit F at the first and second times t_alpha and t_beta, respectively. The position alpha corresponds to the diagram at the top left of FIG. 4 and the position beta corresponds to the diagram at the top right of FIG. 4. The point of intersection C corresponding to the projected position PT in the main plane of the support 20 of the detection element DT is also shown in the bottom diagram of FIG. 4.

The X-ray detection system 2 can further comprise a processing unit 50 configured to determine the projected position PT or C in the main plane of the support (P) of the detection element (DT) based on the two successive times (t_alpha) and (t_beta) determined for the detection element (DT) and the angular speed of rotation of the support V. Specifically, by considering a frame of reference in the space defined by a plane (xOy), with O the intersection of the axis of rotation Δ with the main plane of the support P, and an axis Oz equal to the axis of rotation Δ, the coordinates xc and yc of the projected position of the detection element DT in the main plane of the support P are the solutions to the system of equations:

$$x_C \cos \text{alpha} + y_C \sin \text{alpha} = d \quad \text{[Math. 1]}$$

$$x_C \cos \text{beta} + y_C \sin \text{beta} = d \quad \text{[Math. 2]}$$

where d is the distance between the slit 30 and the axis of rotation Δ, sin represents the trigonometric sine function and cos represents the trigonometric cosine function.

These two equations form a linear system which has a single solution. Specifically, the determinant of this linear system is equal to sin(beta-alpha) and is strictly positive, since the angles alpha and beta are always different because the slit does not pass through the intersection O between the support 20 and the axis of rotation Δ, and because the difference diff=beta-alpha is always strictly smaller than or equal to π.

The angles alpha and beta can be calculated from the measurement of the first and second times t_alpha and t_beta, and from knowing the angular speed of rotation V of the support 20.

The coordinates xc and yc, in other words the position of the projected position C in the main plane of the support P of the detection element DT, can thus be determined based on the equations Math1 and Math2 from the angles alpha and beta. Knowing them makes it possible to determine that the detection element DT is on the straight line passing through the X-ray source 10 and the point C with coordinates xc and yc located in the main plane of the support P. The detection element DT is thus, just by measuring the first and second times t_alpha and t_beta, located two-dimensionally in the main plane of the support P. This then makes it possible to project the position of the detection element DT in a radiological image formation plane, which is located downstream of the detection element DT, by using a projection matrix for the assembly formed by the X-ray source 10 and the collimation device. The mathematical formalism for the projection of an element in such an image formation plane can be found in patent application WO2017072125 (A1). This projected position can be used either for radiological images acquired previously, or in real time, in the case where radiological images are acquired simultaneously with the detection of the element DT and the calculation of this projected position.

FIG. 5 schematically shows a detection system 2 according to the second aspect of the present application, depicting an X-ray source 10 in the form of an X-ray tube, a collimator composed of a support made of $CdWO_4$, secured to a motor able to rotate the support 20 about an axis of rotation which, in the case of FIG. 5, is horizontal, a detection element DT based on gallium nitride (GaN) placed in a cylindrical phantom body made of poly(methyl methacrylate) (PMMA), and a processing unit 50 comprising a field-programmable gate array (FPGA).

FIG. 6A schematically illustrates the operating principle of an optical fork for measuring angles.

In one embodiment, the angles alpha and beta can be measured using an optical fork. A second support 20b can be positioned parallel to the main plane of the support P. The second support 20b is secured to or forms an integral part of the support 20. This second support 20b can comprise a series of N openings (hereinafter called windows), which are transparent in the visible or near-infrared ranges, and are uniformly distributed angularly around a circular periphery centered on a point corresponding to the intersection between the second support 20b and the axis Δ of rotation 15. The N windows are indexed with respect to a reference window, which can correspond to a window that is wider (or respectively narrower) than the other windows.

The optical fork is provided with an emitter 21 and a receiver 22 facing one another. The emitter 21 emits a light wave which, when this light wave passes through one of the windows, is picked up by the receiver. An electrical pulse is thus produced when a window allows the signal to pass from the emitter to the detector. The electrical pulse obtained for the reference window will be wider (or respectively narrower) than the electrical pulse received for the other windows if this reference window is wider (or respectively narrower).

When the collimation device 1 is exposed to X-rays from the X-ray source 10 while the support 20 is rotating, a detection element DT is exposed to X-rays passing through the slit 30 at a first angular position alpha and a second angular position beta. The electrical pulses delivered by the optical fork which are the closest in time to the two detection times of DT make it possible to directly determine the angles alpha and beta of the support 20b and therefore of the support 20 by determining the index of the two corresponding windows. The index of a window is determined by counting the number of pulses detected after the reference pulse produced by the reference window. In a configuration mode with N windows, the angles alpha and beta can be known with an accuracy in degrees of 360/N°. Thus, the coordinates xC and yC of the position of the projected position C in the main plane of the support P of the detection element DT can be determined from the values of the angular positions alpha and beta that are measured. This configuration makes the determination of the angles alpha and beta more robust, because this measurement system is independent of possible variations in the speed of rotation of the support 20.

In one variant of this embodiment with an optical fork, the second support 20b can comprise a series with a limited number of indexed windows, for example 360 fully indexed windows. In this variant, the processing unit (50) comprises a system implementing a phase-locked loop (PLL) which makes it possible to obtain an angular resolution greater than that separating two successive detection windows. Specifically, the phase-locked system delivers an electrical signal at a frequency that is a multiple of the frequency of the electrical signal delivered by the optical fork and in phase with the electrical signal delivered by the optical fork. Thus, between two consecutive windows, angularly spaced apart by 1°, the processing unit 50 can generate a signal ten times faster than the frequency of the electrical pulses at the output of the optical fork. This configuration makes the system for measuring the angles alpha and beta more accurate by providing enhanced angular resolution.

FIG. 6B schematically illustrates the operating principle of the phase-locked loop. The signal 61 is the signal delivered by the optical fork (N=13). The signal 62 is the signal delivered by the phase-locked system (signal in phase and with a frequency three times that delivered by the optical fork, i.e. 39 pulses). The signal 63 is the signal delivered by a detection element DT which comprises pulses at the times t_alpha and t_beta. The determination of the angles alpha and beta of the support 20 follows therefrom as illustrated on the last line at the bottom of FIG. 6B: alpha is approximately equal to $(11/39)*360°$ and beta is approximately equal to $(27/39)*360°$.

FIG. 7 shows measurement results for times t_alpha and t_beta, for three different positions of an X-ray detection element DT placed in a phantom body made of PMMA, at respective distances of 4 mm, 7 mm and 12 mm from the axis of rotation Δ. The difference between the times t_alpha and t_beta for the distance of 4 mm is greater than for the distance of 12 mm. Specifically, the closer the detection element DT is to the axis of rotation Δ, the closer its projected position on the main plane of the support P is to the axis of rotation Δ, and the slower the speed of the portion of the slit illuminating this projected position.

FIG. 8 recapitulates the various results for localizing the preceding detection element DT obtained via one embodiment of the locating method according to the invention, implementing the detection system described above. Two speeds of rotation of the support 20 were used (1000 revolutions per minute for the top table of FIGS. 8 and 1500 revolutions per minute for the bottom table of FIG. 8, respectively). The number of fluoroscopic pulses per second is 60 and 38, respectively. The projected positions P1, P2, P3 are the positions determined for three detection elements, respectively. The measurements of the radial distance r from the detection element DT to the axis of rotation Δ are in agreement with the actual distances. Millimeter precision is obtained.

In another aspect of the present application, the processing unit 50 of the X-ray detection system 2 described above can also be configured to determine the distance L between the plane passing through the detection element DT, and parallel to the collimator, and the X-ray source 10 from the measurement of a duration of irradiation $t_{irr}$ of the detection element DT, from the angular speed of rotation of the support V, from the distance $d_{SS}$ between the X-ray source 10 and the support 20 and from the width l of the slit 30. Determining the distance L makes it possible to spatially locate the detection element DT in three dimensions.

By assuming that the X-ray source 10 is divergent, it can be demonstrated that:

$$L=t_{irr}rVd_{SS}/l \qquad \text{[Math. 5]}$$

where $t_{irr}$ represents the duration of irradiation of the detection element DT, $d_{SS}$ is the distance, known by design, between the X-ray source 10 and the support 20 and r is the distance between the projected position C in the main plane of the support P and the intersection of the axis Δ with the support 20. This formula uses the assumption of a divergent X-ray source 10, making it possible to state that the farther the detection element DT is from the X-ray source 10, the longer the duration of irradiation of the detection element DT.

FIG. 9 illustrates the propagation of a planar X-ray flow from the slit 30 of the support 20 irradiated by the X-ray source 10 exhibiting divergence to the detection element $D_T$. The farther the detection element DT is from the X-ray source 10, the more temporally widened the signal received by the detection element DT becomes.

In particular, it is possible to envisage that the detection element DT is a miniaturized X-ray detector fixed to an object T which is movable with respect to the X-ray source 10, such as a surgical instrument, or a catheter. In this case, the detection system 2 can allow a practitioner or an operator to locate in real time and in three dimensions a surgical instrument introduced into a patient's body. For this, the assumption is made that the speed of rotation V of the support 20 is very high with respect to the speed of movement of the object T being tracked. For example, the detection element DT can be a probe with an external diameter that is typically smaller than 800 microns, comprising a radioluminescent GaN transducer optically coupled to an optical fiber, where the optical fiber is itself connected by its other end to a photo-detection module operated in "photon-counting" mode.

In one or more embodiments, the X-ray source 10 is a pulsed source configured to emit X-rays in emission cycles composed of two modes used alternately, one being an X-ray emission mode, the other being an X-ray non-emission mode. The detection element DT is then configured to detect X-rays passing through the slit 30 in a manner synchronized with the X-ray emission cycles. In this case, it is possible in particular to choose the speed of rotation of the support 20 so that the support 20 makes one revolution over the duration of firing of the pulsed source, that is to say the duration of the X-ray emission mode. This duration of emission can last from a few milliseconds to a few tens of milliseconds. An angular speed V of the support 20 is adjusted to 3000 revolutions per minute for durations of emission of 20 milliseconds.

For example, the support 20 can be made of an X-ray scintillator material, configured to emit scintillation photons when the support 20 is exposed to the X-ray source. The scintillator material can be selected from $CdWO_4$, LSO, LYSO and BGO or any other material with a high atomic number. The thickness of the support 20 can be between 0.5 and 4 mm, depending on the desired X-ray attenuation. In this case, the detection system 2 further comprises a photodiode PD configured to detect the scintillation photons and issue a photocurrent resulting from the detected scintillation photons. One example of a photodiode PD that can be used is the optical switch OPL551 sold by Farnell. The detection of the scintillation photons by the photodiode makes it possible to trigger the acquisition, by the detection element DT, of X-rays passing through the slit 30. In other words, only those X-rays for which the scintillation of the support 20 is detected are detected. This can, for example, be used to subtract a background level determined when the element DT is not being irradiated (i.e. in the absence of scintillation of the support) in order to improve detection contrast and facilitate the choice of detection threshold to reduce false detections.

In the configuration described above, the processing unit 50 can use the photocurrent issued by the photodiode to automatically feedback-control the angular speed of rotation of the support V with respect to the duration of the emission modes of the pulsed source. Thus, the detection element DT detects X-rays only when the X-ray source 10 is in X-ray emission mode, which makes it possible to avoid the noise that exists in the absence of emission by the X-ray source 10.

FIG. 10 schematically shows an X-ray imaging system 3. This X-ray imaging system 3 can implement the X-ray detection system 2 according to any one of the embodiments described in this document. Such an imaging system 3 is intended to produce radiographic images, in particular of parts of a patient's body. Such an imaging system 3 comprises a plurality of acquisition elements Mi forming an acquisition matrix M placed in the acquisition field of the imaging system 3. Each element Mi of the acquisition matrix M can acquire, through integration, an X-ray flow, transmitted through the slit and/or through the support 20 when the support 20 is chosen so as to be partially radiotransparent, when the support 20 of the collimator of the detection system is rotating about its axis Δ. It is thus possible to reconstruct images in two different ways: either after one or more rotations of the slit (radial scanning) a fluoroscopic image is obtained for, or else by using a support whose radiopacity is adjusted so as to let enough X-rays pass through to be able to reconstruct a—possibly degraded—image. These two modes of image acquisition in one imaging plane can be used in combination with the method for detecting the position of a detection element DT, placed upstream in another plane, as described in this document. The quality of the image obtained will depend in particular on the number of rotations of the support used for the acquisition of each image, on the material used for the support and its thickness. By coupling one of these image acquisition modes with the method for detecting the position of a detection element DT, it is possible to locate in real time the detection element DT in a (possibly degraded) image.

The acquisition matrix M can thus acquire a radiographic image on the basis of the acquisitions made respectively by the acquisition elements Mi constituting the acquisition matrix M during a given time period. It should be noted that the rate of the imaging solution presented here is not sufficient for monitoring a surgical instrument, such as a catheter, but allows slow updating of preoperative images. One example of an acquisition matrix M can be the Pixium 3040 model from THALES, with dimensions of 293×398 mm, a resolution of 1904×2586 pixels, and the pixels of which are 154 microns in size.

In FIG. 10, it can be seen that the imaging system 3 comprises a detection system as described above and an acquisition matrix M placed in an imaging plane downstream of the phantom body. It can be seen that the acquisition matrix M is irradiated by the X-ray flow that has passed through the phantom body made of PMMA.

In one or more embodiments, the X-ray imaging system 3 comprises a planar diaphragm 21 placed between the X-ray source 10 and the support 20, delimiting a field of view whose projection FOV on the acquisition matrix M does not exceed the size of the acquisition matrix M. For example, for a square field FOV of 30 cm by 30 cm and a magnification of 3, a planar diaphragm 21 will consist of two pairs of "jaws" forming a square field of 10 cm by 10 cm. Typically, the distance between the X-ray source 10 and the acquisition matrix M, placed behind the patient but at a relatively close distance, is equal to 100 cm. Typically, the distance between the X-ray source 10 and the support 20 is 40 cm. Typically, the distance between the X-ray source 10 and the planar diaphragm 21 is 35 cm. Typically, the distance between the X-ray source 10 and a detection element DT introduced into a patient's body is 80 cm. In general, the detector is rectangular in shape and the diaphragm is also rectangular. In these embodiments, the path the X-rays take is in the following order: source-diaphragm-rotating single-slit collimator-patient with catheter provided with a detection element DT-2D X-ray detector (for example, pixel matrix) for the acquisition of one or more images.

Such an imaging system 3 not only makes it possible to control patients' irradiation dose, but also to couple both the production of radiographic images and the three-dimensional locating, in real time, of a surgical element used for a medical operation implementing an X-ray imaging system. Such an element is, for example, a catheter inserted into a patient's body in a catheterization operation.

FIG. 11 illustrates a plurality of successive angular positions of the support 20 and therefore of the slit 30 which are obtained by rotating the support 20 over time. Thus, the slit 30 produces an irradiation scan of the projection FOV on the acquisition matrix M, from the intersection at each time between the X-ray flow from the slit 30 and the projection FOV on the acquisition matrix M.

In the case of the use of a pulsed source, configured to emit X-rays in emission cycles composed of two modes used alternately, one being an X-ray emission mode, the other being an X-ray non-emission mode, the acquisition matrix M is configured to acquire radiographic images in a manner synchronized with the X-ray emission cycles.

In particular, in the case where the support 20 is made of an X-ray scintillator material, and can emit scintillation photons when it is exposed to the X-ray source, and in the case where the detection system further comprises a photodiode PD that can detect the scintillation photons and issue a photocurrent resulting from the detected scintillation photons, the detection of the scintillation photons by the photodiode makes it possible to trigger the acquisition by the acquisition matrix M of at least one of the X-ray images. Thus, the acquisition by the acquisition matrix M of radiographic images is windowed, the windows corresponding to the different X-ray emission modes by the X-ray source 10. Each radiographic image acquired by the acquisition matrix M originates from a build-up of X-rays over a plurality of emission cycles of the X-ray source 10. This allows the acquisition matrix M to detect only those X-rays from the X-ray source 10, and to avoid detecting any noise that could degrade the quality of the radiographic images acquired by the acquisition matrix M.

In addition, the processing unit can use the photocurrent issued by the photodiode PD to automatically feedback-control the angular speed of rotation of the support V with respect to the duration of the pulses from the pulsed source. This makes it possible to ensure that the support has completed at least one revolution over the duration of a pulse without requiring any interconnection between the processing unit and the X-ray generation system.

FIG. 12 shows three radiographic images obtained via one embodiment of the X-ray imaging method according to the invention, implementing an imaging system 3 as described above. Each of the images corresponds to a position of a miniaturized detection element DT positioned, from left to right in FIG. 12, respectively at 12 mm, 7 mm and 4 mm from the axis of rotation Δ. In each of the three images, it is possible to see a black disk in the center. This black disk is characteristic of the distance d at which the slit 30 on the support 20 is positioned. This black disk, or dead zone, is surrounded by a very bright halo corresponding to the locations of the slit where it is tangent to the black disk: specifically, at these locations, the speed of rotation of the support 20 is slowest, which has the effect of irradiating the slit 30 for a longer period. Beyond this bright halo, brightness decreases in the direction of the periphery of the support 20.

Thus, the invention has the advantage of being able to couple two modes of an X-ray imaging system 3: a mode for locating and tracking objects, such as surgical instruments in a body, "in real time", and a "low-rate" imaging mode, making it possible to produce radiographic images with lower X-ray doses by virtue of the low radiotransparency of the collimation device according to the invention. Another advantage lies in the use of simplified equipment (a single-slit collimator).

Improvements to the collimation device 2 and to the detection 2 and imaging systems 3 as well as to the associated locating and imaging methods are possible by optimizing the geometry of the slit, both in the main plane of the support P and in the thickness of the support 20, in order to further reduce the irradiation dose for patients and practitioners.

For example, this reduction could be achieved by attenuating the very bright halo visible at the periphery of the dead zone present in the images obtained via the imaging method according to the invention and described above.

One embodiment of a slit 30 for attenuating the bright halo and decreasing the irradiation dose could be the use of a slit 30 that is shallower, that is to say one that keeps a thickness of radiopaque material in the vicinity of the axis of rotation Δ of the support 20, over a portion 30a, and which would be deeper, or even cut into the support 20, that is to say passes through the material of the support 20 in the vicinity of the edge of the support 20, over a portion 30b.

Another embodiment of a slit 30 for attenuating the bright halo and decreasing the irradiation dose would be to define a slit 30 that is off-centered by a distance d from the axis of rotation Δ as described in the present application in three regions: two slit segments 301 and 302 separated by a second distance d' from the point of tangency of the slit 30 with a circle of radius d centered on the projection of the axis of rotation of the support Δ on the support 20, and a radiopaque (or less radiotransparent) central portion 303.

FIG. 13 schematically illustrates a collimation device with such a slit 30. In FIG. 13, a support 20 in the form of a disk is shown. The support 20 comprises a slit 30 that is off-centered by a distance R with respect to the axis of rotation Δ made up of two slit segments 301 and 302, each separated by a second distance dd' from the point of tangency of the slit 30, and a central portion 303. The two slit segments 301 and 302 exhibit partial radiotransparency. The central portion 303 exhibits zero radiotransparency.

In one embodiment of the collimation device, the main plane of the support, containing the slit, can further contain one or more holes or channels: these channels are used to calibrate the collimation device within an imaging system according to any one of the embodiments described in this document. The channels make it possible to determine the projection matrix from the main plane of the support to the image acquisition plane (also called the image plane). Thus, the position of a detection element, initially calculated in the main plane of the support of the collimation device 1, can be determined in the image plane by applying this projection matrix.

This projection matrix gathers the geometric location information for the plane of the support with respect to the source and the X-ray detector of the imaging system. For this, before proceeding to the phase of searching for the position of a detection element, at least one image is acquired in which will appear not only the projection of the slit, but also the projection of each channel, the latter being formed by the X-rays passing through the channel in question and arriving at the image plane.

The properties of the channels can be as follows. The diameter is chosen so as to avoid irradiating the patient overly while being sufficient to allow the X-rays to pass through in order to reliably detect the projection of a channel in the image plane. The diameter of the channels is, for example, of the same order of magnitude as the width of the slit. The channels can be positioned at the edge of the plane of the support for the slit in order to obtain better calibration accuracy. The position of each of the channels in the main plane of the support of the collimation device is known.

When the support comprises a plurality of channels, the channels must be distinguishable from one another. For this, the channels can have different diameters or be positioned so that the arrangement formed makes it possible to distinguish them. In addition, the channels should not be aligned: for example, if the main plane of the support has four channels, they should form a quadrilateral. FIG. 14A illustrates one embodiment of a single-slit 20 collimation device 1 with four channels 50A, 50B, 50C, 50D with distinct diameters.

In another embodiment illustrated in FIG. 14B, the plane of the support containing the slit 20 contains a single channel 50E with the properties described above. Since the plane can be rotated, the presence of at least three other channels can be simulated by rotating the collimation device by a known angle each time and acquiring an image for each angle. This embodiment has a number of advantages. There are fewer channels in the plane and therefore fewer X-rays that can reach the patient during the phase of locating the detection element. The problem of distinguishing the projection of the channels on the image plane no longer arises: each image is acquired after rotating the support of the collimation device. Each new position of the channel in the main plane of the support, which is known, is therefore associated with its projected position in the image plane. Since only the plane of the support rotates, and no other element moves, the assembly can be calibrated.

The calibration method that can be used in this context with a view to determining the projection matrix from the plane of the support to the image acquisition plane can be that described in patent application FR3028039A1 or WO2016071645A1. In this calibration method, the position in the image plane of the projections of at least N channels is determined from one or more acquired images. The intrinsic calibration matrix for the "imaging+collimator" system in a reference position and the projected position of the channels in the image plane for this reference position are obtained. A homography is then calculated between the projected position of the channels in the reference and measurement positions, by matching up each channel. For this, the assumption is made that between the reference position and the measurement position, the "source+collimator" assembly is rigidly connected and they therefore do not move with respect to one another. Only the image detector is allowed to move freely relative to the "source+collimator" assembly between the reference and measurement positions. The number N of channels used for calibration must be sufficient to determine the homography. For example, there are at least 4 channels (N=4). In the case where the "source+collimator" assembly is not rigidly connected, other methods are used to project the position of the detection element expressed in the plane of the support to the image plane. For example, the intrinsic calibration matrix for the imaging system in the measurement position is obtained via off-line calibration using a known 3D test pattern and by assuming that the imaging system is mechanically reproducible within a known time interval. More details are given in patent application WO2016071645A1.

The invention claimed is:

1. Collimation device for an X-ray detection system, the collimation device comprising:

a collimator comprising a substantially planar support made of a material with partial or zero radiotransparency, the support being rotatably movable about an axis of rotation ($\Delta$) which passes through the support and which is perpendicular to a first face of the support which acts as an X-ray plane of incidence referred to as the main plane of the support (P), the support (D) being provided on the first face with a single slit which is completely transparent to X-rays and which is configured to generate an X-ray flow when the collimator is exposed to an X-ray source, the slit extending longitudinally in the main plane of the support along an axis located at a non-zero distance (d) from the axis of rotation ($\Delta$), said slit extending through the entire thickness of the support.

2. The collimation device as claimed in claim 1, in which the slit has a projection of rectangular or trapezoidal shape in the main plane of the support (P).

3. An X-ray detection system, the detection system comprising an X-ray source configured to emit an X-ray beam;
a collimation device as claimed in any one of the preceding claims, placed so as to receive the X-ray beam on the plane of incidence of the support;
a drive device configured to rotate the support of the collimation device about its axis ($\Delta$) with a fixed angular speed of rotation (V);
at least one X-ray detection element placed in an acquisition field opposite the support with respect to the X-ray source so as to acquire X-rays when a portion of the X-ray beam, passing through the slit in the support from the first face of the support to the opposite face, reaches the considered detection element during the rotation of the support.

4. The detection system as claimed in claim 3, wherein one detection element (DT) from among said at least one X-ray detection element is configured to detect X-rays passing through the slit at two successive times while the support is rotating, a first time ($t\_alpha$) corresponding to a first angular position (alpha) of the slit and a second time ($t\_beta$) corresponding to a second angular position (beta) of the slit, the first and second angular positions defining in the main plane of the support (P) a point of intersection (C) corresponding to the projected position (PT) in the main plane of the support of the detection element (DT);

the detection system comprising a processing unit configured to determine the projected position (C) in the main plane of the support (P) of the detection element (DT) from the first and second angular positions.

5. The detection system as claimed in claim 4, the processing unit being configured to determine the first and second angular positions based on the first and second times and the angular speed of the support.

6. The detection system as claimed in claim 4, further comprising
    a second support secured to the support or forming an integral part of the support, comprising a series of N windows uniformly distributed angularly around a circular periphery centered with respect to the axis of rotation (Δ) of the support, said series of N windows comprising a reference window of different size from the other windows, the other windows being indexed with respect to this reference window,
    an optical fork, the optical fork being provided with an emitter configured to emit a light wave and a detector configured to detect the light wave, said fork being configured to generate electrical pulses when, on any one of the windows passing between the emitter and the receiver, the receiver receives the light wave,
the processing unit being configured to determine the first and second angular positions based on the indexes of the two windows that have produced the electrical pulses which are temporally closest to the two successive times for which the detection by the detection element (DT) has taken place.

7. The detection system as claimed in claim 4, wherein the processing unit is configured to:
    determine the distance between a plane passing through the detection element (DT) and parallel to the main plane of the support (P) and the X-ray source, in the case where the slit is rectangular in shape, from a duration of irradiation of the detection element (DT), from the angular speed of rotation of the support (V), from the distance (D) between the X-ray source and the support and from the width of the slit (I) and from the distance r between the intersection of the axis of rotation (Δ) of the support and the projected position (C) in the main plane (P) of the support.

8. The detection system as claimed in claim 4, wherein:
the X-ray source is a pulsed source configured to emit X-rays in emission cycles composed of two modes used alternately, one being an X-ray emission mode, the other being an X-ray non-emission mode
    the detection element (DT) is configured to detect X-rays passing through the slit in a manner synchronized with the X-ray emission cycles.

9. The detection system as claimed in claim 8, wherein the support is made of an X-ray scintillator material, said support being able to emit scintillation photons when the support is exposed to the X-ray source, said detection system further comprising a photodiode (PD) configured to detect scintillation photons and issue a photocurrent resulting from the detected scintillation photons so as to trigger the detection and acquisition by the detection element (DT) of X-rays passing through the slit.

10. The detection system as claimed in claim 9, wherein the processing unit is configured to use the photocurrent issued by the photodiode (PD) to automatically feedback-control the angular speed of rotation of the support (V) with respect to the duration of the pulses from the pulsed source.

11. An X-ray imaging system comprising: a detection system as claimed in claim 4; a plurality of acquisition elements forming an acquisition matrix (M) placed in an acquisition field of the imaging system, each element of the acquisition matrix (M) being configured to acquire an X-ray flow build-up when the support of the collimator of the detection system is rotating about its axis (Δ), the acquisition matrix (M) being configured to acquire a radiographic image on the basis of the acquisitions made respectively by the acquisition elements constituting the acquisition matrix (M) during a given time period.

12. The X-ray imaging system as claimed in claim 11, further comprising:
a planar diaphragm placed between the X-ray source and the support, delimiting a field of view whose projection on the acquisition matrix (M) does not exceed the size of the acquisition matrix (M).

13. The X-ray imaging system as claimed in claim 11, wherein:
    the X-ray source is a pulsed source configured to emit X-rays in emission cycles composed of two modes used alternately, one being an X-ray emission mode, the other being an X-ray non-emission mode,
    the detection element (DT) is configured to detect X-rays passing through the slit in a manner synchronized with the X-ray emission cycles, and
wherein:
the acquisition matrix (M) is configured to acquire radiographic images in a manner synchronized with the X-ray emission cycles.

14. The X-ray imaging system as claimed in claim 13, wherein the support is made of an X-ray scintillator material, said support being able to emit scintillation photons when the support is exposed to the X-ray source, said detection system further comprising a photodiode (PD) configured to detect scintillation photons and issue a photocurrent resulting from the detected scintillation photons so as to trigger the detection and acquisition by the detection element (DT) of X-rays passing through the slit, and
wherein the photodiode (PD) is configured to detect the scintillation photons and issue a photocurrent resulting from the detected scintillation photons so as to trigger the acquisition by the acquisition matrix (M) of at least one of the radiographic images.

15. The X-ray imaging system as claimed in claim 14, wherein the processing unit is configured to use the photocurrent issued by the photodiode (PD) to automatically feedback-control the angular speed of rotation of the support (V) with respect to the duration of the pulses from the pulsed source, and wherein the processing unit is configured to use the photocurrent issued by the photodiode (PD) to automatically feedback-control the angular speed of rotation of the support (V) with respect to the duration of the pulses from the pulsed source.

16. A method for locating a detection element (DT) of an X-ray detection system as claimed in claim 4, the method comprising the following steps:
    rotating the support of the collimation device about its axis of rotation (Δ) at a fixed angular speed of rotation (V);
    exposing the support to an X-ray beam from the X-ray source during the rotation of the support;
    the detection element (DT) detecting X-rays passing through the slit in the support at two successive times, a first time (t_alpha) corresponding to a first angular position (alpha) of the slit and a second time (t_beta) corresponding to a second angular position (alpha) of the slit, the processing unit determining the projected position (C) in the main plane (P) of the support of the detection element (DT) based on the first and second angular positions.

17. The locating method as claimed in claim 16, wherein the first and second angular positions are determined on the basis of the first and second times and the angular speed of the support.

18. A method for locating a detection element (DT) of an X-ray detection system as claimed in claim 6, the method comprising the following steps:

rotating the support of the collimation device about its axis of rotation (Δ) at a fixed angular speed of rotation (V);

exposing the assembly formed by the support and the second support to an X-ray beam from the X-ray source during the rotation of the support;

detecting electrical pulses produced when, on any one of the windows passing between the emitter and the receiver of the optical fork, the receiver receives the light wave;

the detection element (DT) detecting X-rays passing through the slit in the support for a first angular position (alpha) of the second support and a second angular position (beta) of the second support, the processing unit determining the projected position (C) in the main plane of the support based on the first and second angular positions, the first and second angular positions being obtained on the basis of the indexes of the two windows that have produced the electrical pulses which are temporally closest to the two successive times for which the detection by the detection element (DT) has taken place.

19. The method for locating a detection element (DT) as claimed in claim 18, in the case where the X-ray detection system is a detection system as claimed in claim 10, wherein the processing unit uses the photocurrent issued by the photodiode (PD) to automatically feedback-control the angular speed of rotation of the support (V) with respect to the duration of the pulses from the pulsed source.

20. The locating method as claimed in claim 16, comprising a step of determining, by the processing unit, the distance (D) between a plane containing the detection element (DT) and parallel to the main plane (P) of the support and the X-ray source from a duration of irradiation (tirr) of the detection element (DT), from the angular speed of rotation of the support (V), from the distance (D) between the X-ray source and the support, from the width of the slit (l) and from the distance r between the intersection of the axis of rotation (Δ) of the support and the projected position (C) in the main plane (P) of the support.

21. An X-ray imaging method, the imaging method being implemented by an X-ray imaging system as claimed in claim 11, the imaging method comprising the following steps:

rotating the support of the collimation device of the imaging system about its axis of rotation (Δ) at a fixed angular speed of rotation (V);

exposing the support to an X-ray beam from the X-ray source during the rotation of the support;

the acquisition elements of the acquisition matrix detecting X-rays during the rotation of the support;

acquiring a radiographic image on the basis of the detections made respectively by the acquisition elements of the detection matrix (M) during a given time period.

22. An X-ray imaging method, the imaging method being implemented by means of an X-ray imaging system as claimed in claim 14, the imaging method comprising the following steps:

rotating the support of the collimation device of the imaging system about its axis of rotation (Δ) at a fixed angular speed of rotation (V);

exposing the support to an X-ray beam from the X-ray source during the rotation of the support;

the acquisition elements of the acquisition matrix detecting X-rays during the rotation of the support;

the support emitting scintillation photons;

the photodiode (PD) detecting the scintillation photons, the photodiode issuing a photocurrent resulting from the detected scintillation photons so as to trigger the acquisition by the acquisition matrix (M) of at least one of the radiographic images, acquiring a radiographic image on the basis of the detections made respectively by the acquisition elements of the detection matrix (M) during a given time period.

23. The X-ray imaging method as claimed in claim 22, the imaging method being implemented by means of an X-ray imaging system, wherein the processing unit uses the photocurrent issued by the photodiode (PD) to automatically feedback-control the angular speed of rotation of the support (V) with respect to the duration of the pulses of the pulsed source such that the acquisition of a radiographic image on the basis of the detections made respectively by the acquisition elements of the acquisition matrix (M) is temporally windowed over the X-ray emission modes of the emission cycles of the pulsed source.

* * * * *